(12) United States Patent
Li et al.

(10) Patent No.: US 11,547,417 B2
(45) Date of Patent: Jan. 10, 2023

(54) LEFT ATRIAL APPENDAGE OCCLUDER

(71) Applicant: Lifetech Scientific (Shenzhen) Co., Ltd., Shenzhen (CN)

(72) Inventors: Anning Li, Shenzhen (CN); Deyuan Zhang, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 700 days.

(21) Appl. No.: 16/373,268

(22) Filed: Apr. 2, 2019

(65) Prior Publication Data

US 2019/0223882 A1  Jul. 25, 2019

Related U.S. Application Data

(60) Continuation of application No. 14/924,458, filed on Oct. 27, 2015, now Pat. No. 10,258,343, which is a division of application No. 14/122,794, filed on Jan. 27, 2014, now Pat. No. 9,808,253.

(51) Int. Cl.
*A61B 17/12* (2006.01)
*A61B 17/00* (2006.01)

(52) U.S. Cl.
CPC .. *A61B 17/12172* (2013.01); *A61B 17/12122* (2013.01); *A61B 17/12177* (2013.01); *A61B 2017/00526* (2013.01); *A61B 2017/12095* (2013.01)

(58) Field of Classification Search
CPC .......... A61B 17/0057; A61B 17/12122; A61B 2017/00575; A61B 17/12177; A61B 17/12172; A61B 2017/1205; A61B 2017/00619; A61B 2017/00606; A61B 2017/00597; A61B 2017/00623; A61B 17/12022–12036; A61B 17/1214; A61M 29/02
See application file for complete search history.

(56) References Cited

U.S. PATENT DOCUMENTS

| | | | |
|---|---|---|---|
| 6,652,556 B1 * | 11/2003 | VanTassel | A61F 2/0105 606/200 |
| 7,708,770 B2 * | 5/2010 | Linder | A61F 2/013 623/1.11 |
| 8,801,746 B1 * | 8/2014 | Kreidler | A61B 17/1215 606/200 |

(Continued)

*Primary Examiner* — Katherine M Shi
*Assistant Examiner* — Mikail A Mannan
(74) *Attorney, Agent, or Firm* — Raymond Sun

(57) ABSTRACT

A left atrial appendage occluder comprises an elastic closure disc, and a supporting structure connecting with the closure disc and being located on one side of the closure disc, with the supporting structure comprising a central end connecting with the closure disc and a plurality of interconnected and bent struts, wherein at least one anchoring thorn is set near the end of at least one strut with the anchoring thorn toward the closure disc. The left atrial appendage occluder has a stable structure, a good positioning and sealing effect on the cavity wall in the left atrial appendage, and it is easy to position repeatedly; it can also be recycled before separating from a conveyor. When in surgical operation, the left atrial appendage occluder can select the position area based on the actual shape and size of the patient's left atrial appendage, so the surgical risk is lowered.

20 Claims, 13 Drawing Sheets

(56) References Cited

U.S. PATENT DOCUMENTS

2009/0112249 A1* 4/2009 Miles ................. A61B 17/1215
 606/192
2010/0324586 A1* 12/2010 Miles ............... A61B 17/12177
 606/198
2010/0324589 A1* 12/2010 Carpenter ......... A61M 25/0015
 606/200

* cited by examiner

LEFT ATRIAL APPENDAGE OCCLUDER

TECHNICAL FIELD

The invention relates to a medical device, and particularly relates to an occluder which is transmitted to a selected part of a human body by the interventional method through catheter technology to prevent stroke symptoms caused by thrombus resulted from left atrial appendage due to atrial fibrillation.

BACKGROUND OF THE INVENTION

Treating diseases by using the interventional method through catheter technology is a therapy applied more and more widely at present. Various materials, devices and medicines are placed into heart and arteriovenous vessels of a human body by the catheter-based interventional therapy.

For example, an occluder (such as, atrial septal defect (ASD) occluder, ventricular septal defect (VSD) occluder, patent ductus arteriosus (PDA) occluder, patent foramen ovale (PFO) occluder, etc.) is placed to a defective part of the heart by the catheter-based interventional method to occlude the defect so as to treat the congenital heart disease. As a well-known device, with the threaded connection between the device and a pusher, the device is conveyed to a predetermined part by the pusher, and then the device and the pusher are disengaged by releasing the threaded connection. For such a device, the threaded connection may realize the reliable and safe connection between the device and the pusher, and may also achieve controllable release. In other words, if the size of the device is improper, or when the device cannot expand well, the device may be accommodated into a delivery catheter again and then replaced with a new device appropriate for repositioning and realizable release.

For another example, an occluder is placed into the left atrial appendage by the catheter-based interventional method in order to prevent thrombus caused by left atrial appendage due to atrial fibrillation that could transfer up to the brain so as to result in stroke, or to prevent the thrombus from reaching other parts of the body through the human blood circulatory system and then resulting in systemic embolism. The occluder is placed into the left atrial appendage in order to occlude the left atrial appendage and block the blood flow entering the left atrial appendage, so that this may eliminate the risk of thrombus caused by the left atrial appendage due to atrial fibrillation and avoid apoplexia. At present, the device is generally connected with an introducer by threads. All the devices may be classified into two categories roughly by their structures: a plug type left atrial appendage occluder shown in FIG. 1 and FIG. 2, and a plug-and-disc type left atrial appendage occluder shown in FIG. 3. In FIGS. 1-3, 1 refers to left atrium (LA); 2 refers to left atrial appendage (LAA); 3 refers to the wall of left atrial appendage cavity; 4 refers to a flow blocking membrane of the plug type left atrial appendage occluder; 5 refers to a main body of the plug type left atrial appendage occluder; 6 refers to a pit-shaped gap between the plug type left atrial appendage occluder and the left atrial appendage; 7 refers to a main body of the plug-and-disc type left atrial appendage occluder; and, 8 refers to a flow blocking membrane of the plug-and-disc type left atrial appendage occluder. The plug type left atrial appendage occluder is made into a spherical, cylindrical or conical plug with a flow blocking membrane. The plug is elastic and may deform in the left atrial appendage to fit with the shape of the left atrial appendage cavity for the purpose of plugging the left atrial appendage, while the flow blocking membrane on the plug may block off the blood flow. The plug-and-disc type left atrial appendage occluder is a complex of a cylindrical plug and a disc-shaped part, and a flow blocking membrane is also sutured onto the disc. The cylindrical plug is placed into the left atrial appendage cavity to fix the whole device. The disc-shaped part covers the entrance of the left atrial appendage and is used for blocking off the blood flow entering the left atrial appendage.

When these devices are placed into the heart, arteriovenous vessels and the left atrial appendage of a human body by the catheter-based interventional method, because the heart and arteriovenous vessels of the human body, and particularly the anatomical structure of the left atrial appendage, are complicated, it is required that a device must reach a predetermined position exactly and fit well with the anatomical structure of the predetermined position, mechanical requirements and dynamic requirements of the blood flow. Therefore, the structure of the device must be designed very precisely. Under the premise of causing minimal damage to the human body, the skin close to a vessel is punctured first, and then a guide wire enters the vessel from the punctured pore. Under the guidance of the guide wire, one end of a catheter reaches the predetermined position, while the other end thereof remains outside of the body. Then, the device is delivered to the predetermined position by the catheter and a pusher. During such an operation, a very small and flexible catheter is required, and the catheter and the guide wire are designed to have good development under the X-ray. Once the catheter reaches the predetermined position, the guide wire is removed, and then the device is guided to the tail end of the catheter by the pusher through a channel built by the catheter. When the device is totally exposed from the tail end of the catheter, the device is detached from the pusher to realize the release of the device.

At present, there are many limitations for the left atrial appendage occluder.

1. The following shows the limitations of the plug type left atrial appendage occluder.

(a) When the device is plugged into the left atrial appendage, the deformability of this device is limited, and the shape of the entrance of the left atrial appendage is very irregular. Therefore, many small pit-shaped gaps 6 are formed between the part attached with membrane and the outer edge of the entrance of the left atrial appendage (as shown in FIG. 2), equivalent to many artificial left atrial appendages formed. Because the entrance of the left atrial appendage cannot be blocked completely, it is difficult to eliminate the thrombus caused by the left atrial appendage due to atrial fibrillation, so that the thrombus endogenus of the "artificial left atrial appendage" device will increase the probability of forming left atrial appendage thrombus.

(b) The anatomical structures of left atrial appendages of all people are in different shapes, such as an oval shape, a peanut shape, etc., and some left atrial appendages have multiple cavities, so the plug type left atrial appendage occluder cannot fit anatomical structures of all left atrial appendages completely and cannot be stably fixed.

(c) The depths of left atrial appendages of all people are different, so the length of the plug type left atrial appendage occluder cannot fit various depths of left atrial appendages.

2. The following shows the limitations of the plug-and-disc type left atrial appendage occluder.

(a) The plug-and-disc type left atrial appendage occluder has a complex body, in which the plug part and the disc part cannot be deformed completely and independently. When the plug is plugged into the left atrial appendage, the shape of the plug needs to comply with the internal structure of the left atrial appendage, so that the disc part will encounter the traction of the plug part when buckled on the entrance of the left atrial appendage. As a result, the disc part cannot fit fully with the entrance of the left atrial appendage. Therefore, the blood flow cannot be blocked completely, and it is difficult to achieve the best occlusion effect.

(b) Because the anatomical structures of left atrial appendages of all people are in different shapes, it is required to find an optimal fixing point in the cavity of the left atrial appendages. Therefore, it is required that the plug part may realize the best fixation in different depths. However, because the lengths of the plug part and the disc part are limited for adjustment, it is difficult for most left atrial appendages to achieve the best fixation and blockage of blood flow.

3. Furthermore, most of left atrial appendage occluders plugged in the left atrial appendage is of a closed structure, so the left atrial appendage occluders are difficult to fit different shapes of cavities of left atrial appendages.

4. In addition, it is required to add an anchor structure on an occluder to fix the left atrial appendage occluder. However, the anchor structures of present products are unreasonable; for example, the anchors of some left atrial appendage occluders are several fine wires equipped on the occluders by suture lines. It is difficult for such an anchor to penetrate through the wall of the left atrial appendage under the condition of compression in the cavity of the left atrial appendage, so that the stable fixation cannot be realized. Besides, the anchors of some left atrial appendage occluders have enough puncture force but pose an obstacle to the withdrawal of an occluder, so that the occluders cannot realize the repeated positioning.

DISCLOSURE OF THE INVENTION

Technical Problems

The technical problem to be solved by the invention is to provide a left atrial appendage occluder blocking the blood flow from flowing into the left atrial appendage with good effect, having stable fixation in the cavity of the left atrial appendage, and the capability of repeatable positioning, in order to solve problems that a left atrial appendage occluder in the prior art cannot achieve the best occlusion effect and that its fixation in the cavity of the left atrial appendage is unstable; and that it fails to realize the repeated positioning, etc.

Solutions

Technical Solutions

Technical solutions employed to solve the technical problems of the invention are as below: a left atrial appendage occluder is provided, comprising an elastic closure disc. The left atrial appendage occluder also comprises an elastic fixing frame connected with the closure disc and located on one side of the closure disc. The fixing frame comprises a central end connected with the closure disc and a plurality of interconnected and bent struts, wherein at least one anchor is set near the end of at least one strut with the anchor pointing toward the closure disc.

As a further improvement of the invention, the central end of the fixing frame further comprises a flexible connection structure, and the fixing frame is connected with the closure disc via the flexible connection structure.

As a further improvement of the invention, the flexible connection structure is a flexible connector with an elastic spiral.

As a further improvement of the invention, the flexible connection structure is a spring.

As a further improvement of the invention, the flexible connection structure is a multi-strand flexible member.

As a further improvement of the invention, the closure disc is a mesh with two fixed ends, and a flow blocking membrane is disposed on the closure disc.

As a further improvement of the invention, the flow blocking membrane is made of PET or PTFE material.

As a further improvement of the invention, the root of the anchor on the strut is disposed on the struts while the tip thereof is splayed outward automatically, and the anchor is retracted back to the struts when it is compressed.

As a further improvement of the invention, the length of the anchor on the strut is 1-2 mm.

As a further improvement of the invention, the tail ends of the struts are provided with bulbs.

As a further improvement of the invention, a U-shaped bent part is provided between the tail end of the strut and the anchor.

As a further improvement of the invention, one end of the closure disc is provided with a connecting member with threads connected with an introducer, while the other end thereof is connected to the fixing frame.

As a further improvement of the invention, the closure disc and the fixing frame are made of nickel titanium alloy.

As a further improvement of the invention, the fixing frame is formed by cutting one nickel titanium tube and then heat treating for shaping.

As a further improvement of the invention, the struts on the fixing frame are symmetrically arrayed in radial, radiated from the central end in the direction of the oblique axis and expanded like an umbrella, and then a section of the struts is bent to be essentially parallel to a central axis of the fixing frame.

Advantages of the Invention

Advantages

Compared with the prior art, the invention has the following advantages:

1. The left atrial appendage occluder has a stable structure and can fit various structures and various sizes of the cavity of the left atrial appendage to the largest extent.

2. It allows positioning on the wall of the left atrial appendage more stably and seals the entrance of the left atrial appendage more closely, considering the balance between the positioning and sealing effects.

3. The left atrial appendage occluder is easy to position repeatedly and may be withdrawn before being detached from an introducer. When in surgical operation, a position area is selected based on the actual shape and size of the patient's left atrial appendage, so selection of an improper position area caused by limitations of the device can be avoided and the surgical risk is lowered.

4. The operating steps are simple and smooth, so the times of repeated positioning by a doctor is reduced to the largest extent, and the harm to a patient is lowered.

5. The left atrial appendage occluder can fit a small sheath canal, and so the damage of the sheath canal to the patient's vascular wall is lowered.

BRIEF DESCRIPTION OF THE DRAWINGS

The invention is further described as below with reference to drawings and embodiments. In the drawings.

IMPLEMENTATION OF THE OPTIMAL EMBODIMENTS

Optimal Embodiments

To make the purposes, technical solutions and advantages of the invention understood more clearly, the invention is further described as below in details by embodiments with reference to drawings. It should be understood that the specific embodiments described herein are provided just for the purpose of explanation of the invention, but not intended to limit the invention.

The invention is further described as below in details by multiple specific embodiments with reference to drawings.

First Embodiment

Figure 6:
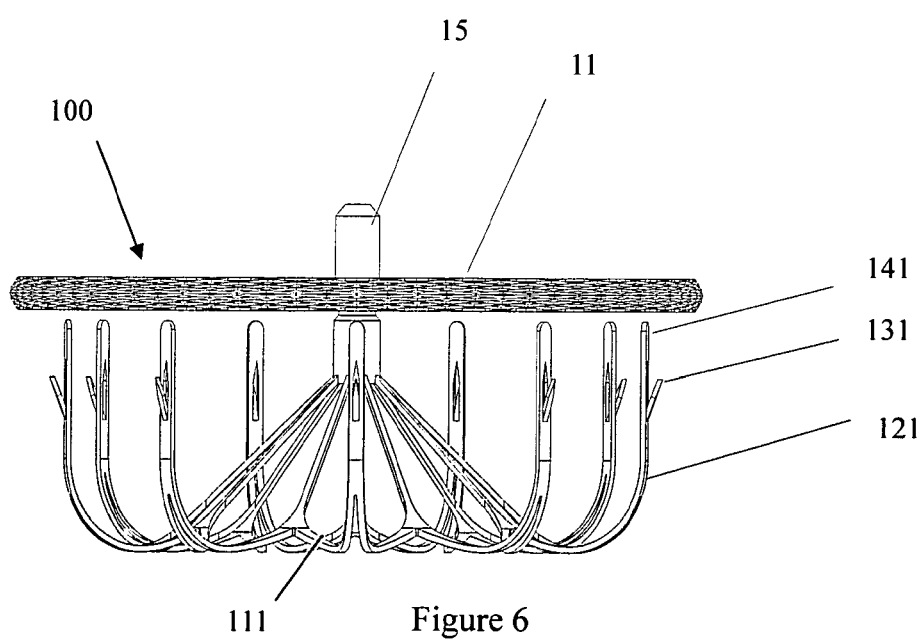
FIG. 6 is a main view of a left atrial appendage occluder according to a first embodiment of the present invention.
Figure 7:
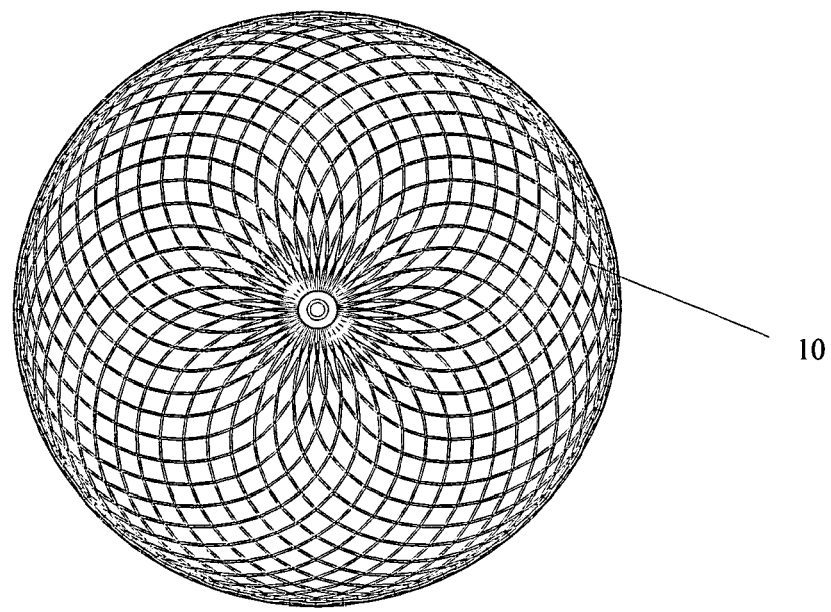
FIG. 7 is a top view of a left atrial appendage occluder according to a first embodiment of the present invention.
Figure 8:
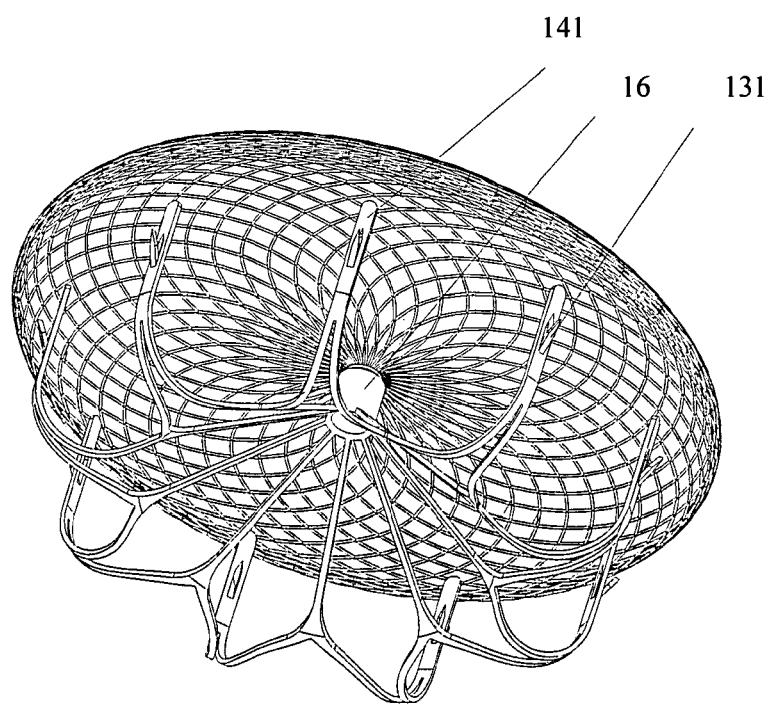
FIG. 8 is a perspective diagram of a left atrial appendage occluder according to a first embodiment of the present invention.

As shown FIG. 6, FIG. 7 and FIG. 8, the left atrial appendage occluder 100 in the first embodiment of the invention comprises a closure disc 11 and a fixing frame 111 connected with the closure disc 11. The fixing frame 111 comprises a plurality of interconnected struts 121. The fixing frame 111 is in a shape as shown in FIG. 6 formed by cutting a nickel titanium tube into a plurality of interconnected struts 121, stretching via a die and then heat treating for shaping. The closure disc 11 is made into a mesh grid 10 via nickel titanium wires by weaving, and then made into a disc shape by heat treatment. Two ends of the closure disc are fixed by sleeves. Then, the sleeve at one end is welded with a connecting member 15 with threads connected with a conveyor, while the other end of the closure disc 11 is a fixed end having its sleeve connected with a connector 16 on the fixing frame 111. Inside the closure disc 11, a flow blocking membrane (PTFE or PET membrane) is sutured via medical suture lines. Refer to FIG. 7 for the top view of the closure disc 11. Although nine struts 121 are employed in the first embodiment, another number may be selected according to mechanical performance and size standard requirements, for example, six, eight, twelve, sixteen, etc. Those nine struts 121 are arrayed symmetrically in radial fashion and splayed like an umbrella from the center along the direction of the oblique axis. Then, tail ends 141 of the struts 121 are basically parallel to the central axis of the fixing frame 111 through U-shaped bending. Each of the struts 121 is divided into two branches at the bent part. Two branches of two adjacent struts 121 are connected into a whole through U-shaped bending and finally gathered onto the connector 16 of the fixing frame 111. The connector 16 is at one end which is not cut apart of the nickel titanium tube, and located at the center of the fixing frame 111 to form a central end connected with the closure disc 11. During the cutting, an anchor 131 at the tail end 141 of the strut 121 will also be provided by cutting. By using a corresponding die to shape the anchor 131, the anchor 131 points toward the tail end 141 of the strut 121. The root of the anchor 131 is located on the strut 121, while the tip of the anchor 131 thereof is expanded outward automatically. After being compressed, the anchor 131 is retracted onto the strut 121. The length of the anchor 131 is sized and configured, not only to ensure enough fixing effect, but also not to add risk due to an excessively large penetration depth in the left atrial appendage; for example, 1-2 mm of the anchor in length. Finally, the fixed end of the closure disc 11 and the connector 16 of the fixing frame 111 are welded together. The closure disc 11 has good flexibility, while the struts 121 have certain deformability, so that they may play a role in adjusting relative positions and relative distances between the closure disc 11 and the fixing frame 111 to a certain extent. Thus, the anchor 131 on the struts 121 points toward the closure disc 11 and may pin at different depths into the left atrial appendage, and the seal of the closure 11 to the entrance of the left atrial appendage is ensured.

Second Embodiment

Figure 9:
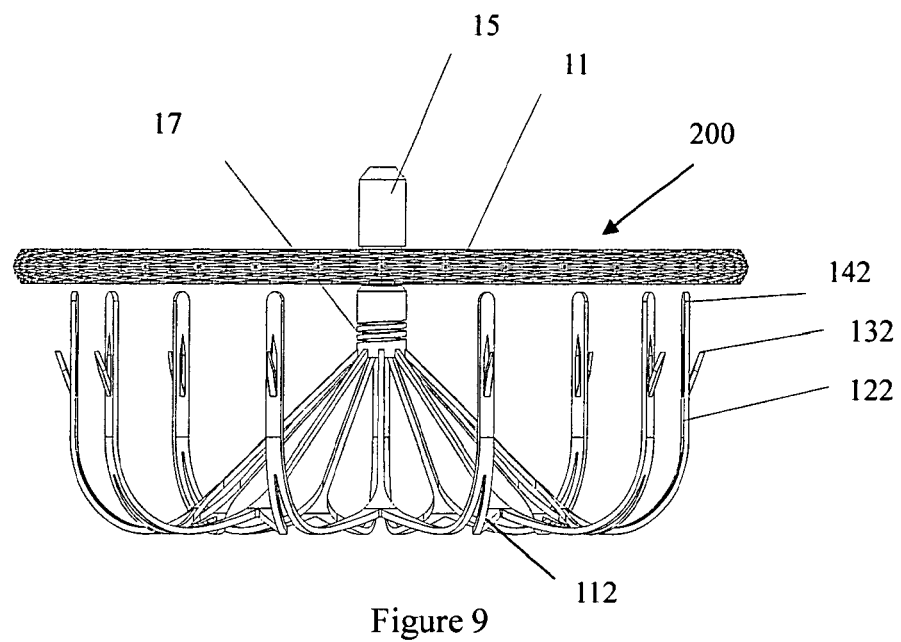
FIG. 9 is a main view of a left atrial appendage occluder according to a second embodiment of the present invention.
Figure 10:
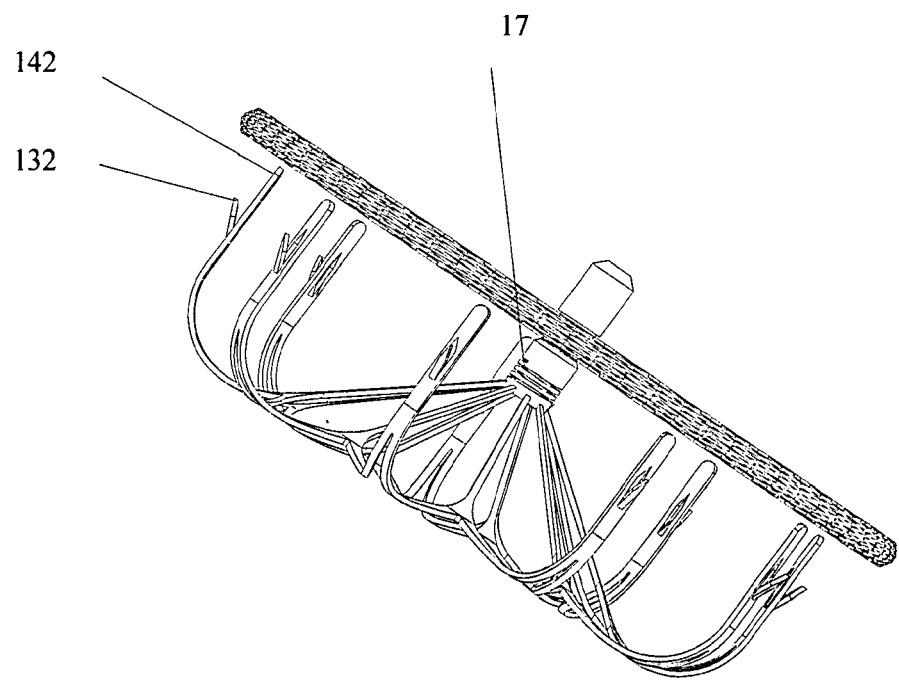
FIG. 10 is a perspective diagram of a left atrial appendage occluder according to a second embodiment of the present invention.
Figure 11:
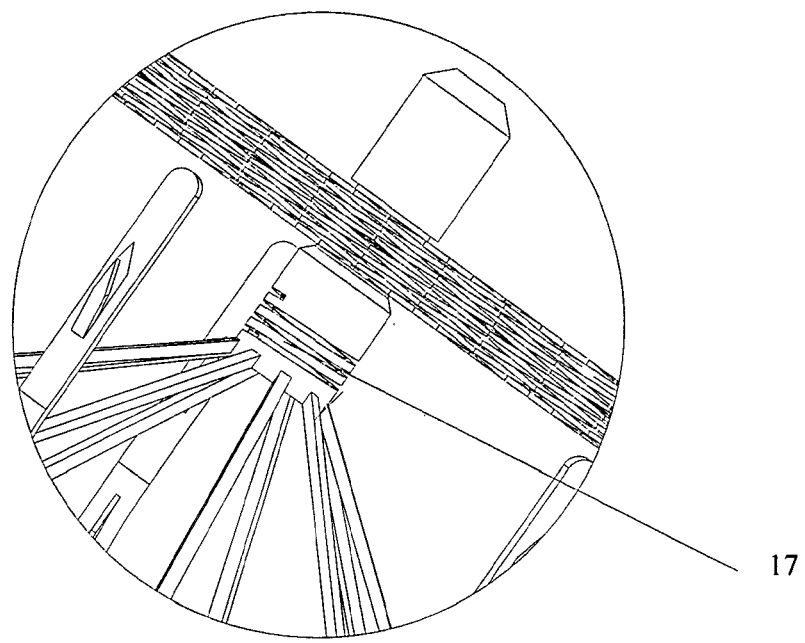
FIG. 11 is a partial enlarged view of part of FIG. 10.
Figure 12:
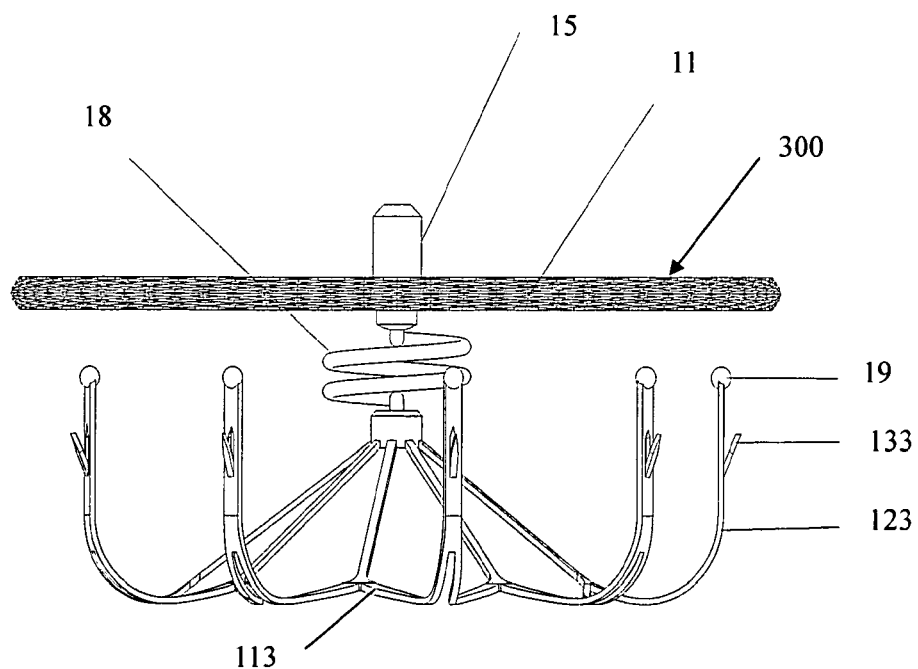
FIG. 12 is a main view of a left atrial appendage occluder according to a third embodiment of the present invention.
Figure 13:
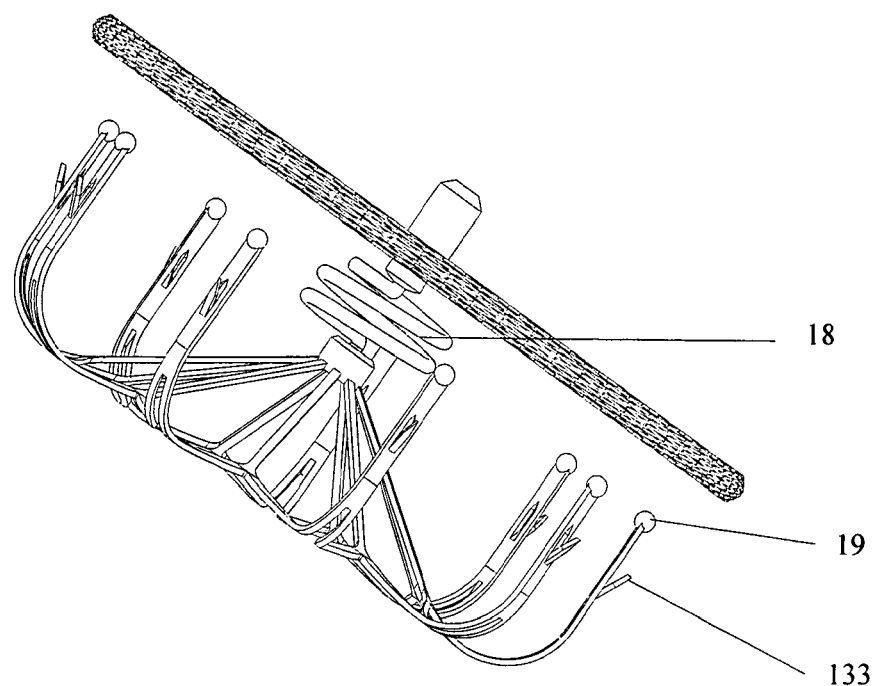
FIG. 13 is a perspective diagram of a left atrial appendage occluder according to a third embodiment of the present invention.

As shown in FIG. 9, FIG. 10 and FIG. 11, the left atrial appendage occluder 200 in the second embodiment of the invention comprises a closure disc 11 and a fixing frame 112 connected with the closure disc 11. The closure disc 11 is made into a mesh shape via nickel titanium wires by weaving, and then made into a disc shape by heat treatment. Two ends thereof are fixed by sleeves. The sleeve at one end is welded with a connecting member 15 with threads connected with a conveyor. Then, a flow blocking membrane (PTFE or PET membrane) is sutured inside the closure disc 11 via medical suture lines. The other end of the closure disc 11 is a fixed end. The sleeve of the fixed end is connected with a central end of the fixing frame 112. The central end comprises a flexible connector 17. The top view of the closure disc 11 is the same as shown in FIG. 7 in the first embodiment. Struts 122 of the fixing frame 112 are formed by cutting nickel titanium tubes and heat treating them for shaping. During the cutting, the anchor 132 on the fixing frame 112 will also be provided by cutting. The shape of the anchor 132 is formed by a corresponding die, and the anchor 132 points toward the tail end 142 of the strut 122. When cutting the nickel titanium tubes, the flexible connector 17 will also be formed by cutting. The flexible connector 17 comprises an elastic spiral structure which is located between the sleeve at the fixed end of the closure disc 11 and the struts 122 of the fixing frame 112. The flexible connector is as shown in FIG. 11 after partial enlargement. Finally, the sleeve at the fixed end of the closure disc 11 and the flexible connector 17 of the fixing frame 112 are connected together by welding. The flexible connector 17 has better deformability and may adjust the relative positions and relative distances between the closure disc 11 and the fixing frame 112 within a larger scope. Thus, the anchor 132 of the strut 122 points towards the closure disc 11 and can stably pin at different depths in the left atrial appendage, and the seal of the closure 11 to the entrance of the left atrial appendage is ensured.

Third Embodiment

Figure 5:
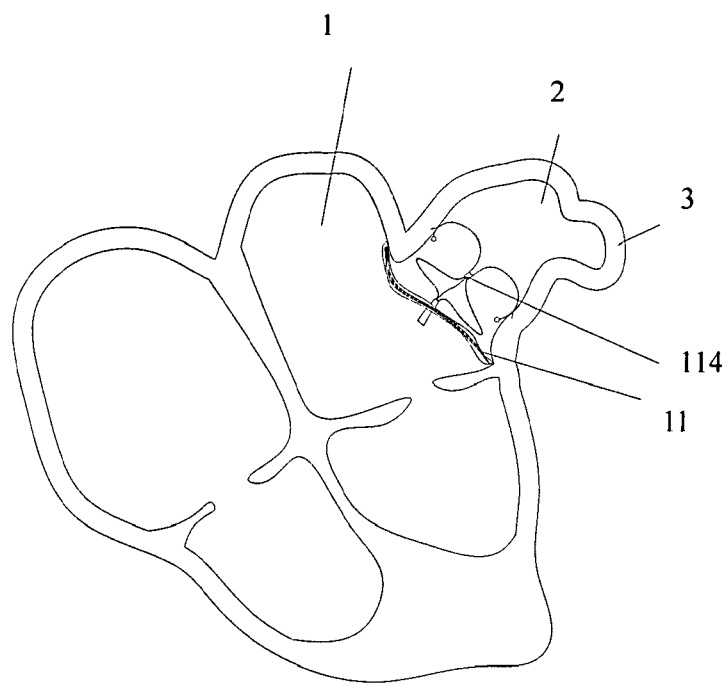
FIG. 5 is a schematic diagram of a position of a left atrial appendage occluder of the invention in an anatomical structure of a heart and a left atrial appendage, in which a fixing frame pins on a shallow position of the left atrial appendage.
Figure 14:
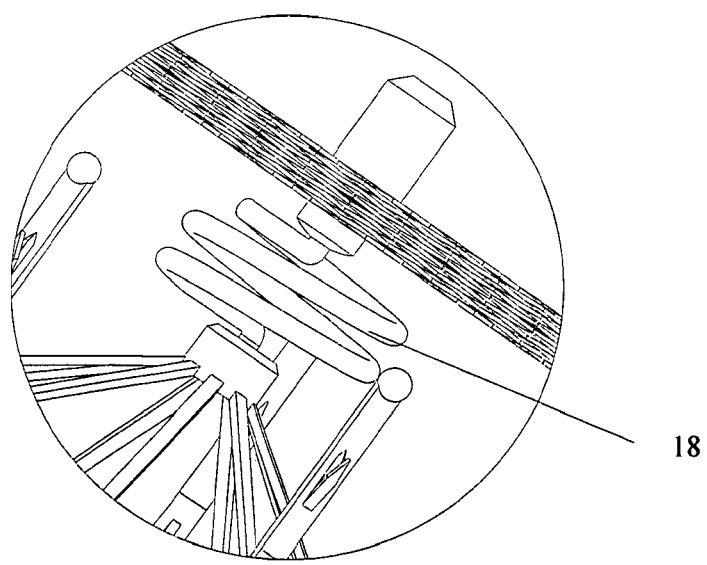
FIG. 14 is a partial enlarged view of part of FIG. 13.
Figure 15:
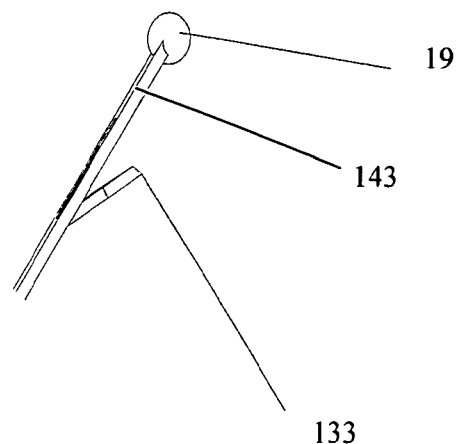
FIG. 15 is an enlarged diagram of the tail ends of struts on a fixing frame in FIG. 13.

As shown in FIG. 12 to FIG. 15, the left atrial appendage occluder 300 in the third embodiment of the invention comprises a closure disc 11 and a fixing frame 113 connected with the closure disc 11. The closure disc 11 is made into a mesh shape via nickel titanium wires by weaving, and then made into a disc shape by heat treatment. Two ends thereof are fixed by sleeves. The sleeve at one end is welded with a connecting member 15 with threads connected with a conveyor. Then, a flow blocking membrane (PTFE or PET membrane) is sutured inside the closure disc 11 via medical suture lines. The other end of the closure disc 11 is a fixed end. The sleeve of the fixed end is connected with a central end of the fixing frame 113. The central end comprises a connecting spring 18. The top view of the closure disc 11 is the same as shown in FIG. 7 in the first embodiment. Struts 123 of the fixing frame 113 are shaped by cutting and heat treating nickel titanium tubes. Tail ends of the struts 123 are made into bulbs 19 by hot melting, as shown in FIG. 5, to lower the damage of the occluder to the left atrial appendage. During the cutting, the anchor 133 on the fixing frame 113 will also be provided by cutting. The shape of the anchor 133 is formed by a corresponding die, and the anchor 133 points toward the tail end 143 of the strut 123. When cutting the nickel titanium tube, a short section of the nickel titanium tube still remains at the other end of the fixing frame 113 away from the bulb 19, to avoid the separation of the struts 123 from each other at this end. The connecting spring 18 forms a spiral structure via single or multiple nickel titanium wires by heat treatment, which is as shown in FIG. 14 after partial enlargement. Finally, the closure disc 11 and the fixing frame 113 are connected together by the connecting spring 18. One end of the connecting spring 18 is welded with the sleeve at the fixed end of the closure disc 11, while the other end of the connecting spring 18 is welded with the end of the fixing frame 113 where the nickel titanium tube remains uncut. The connecting spring 18 has strong deformability and may adjust the relative positions and relative distances between the closure disc 11 and the fixing frame 113 to a large extent. Thus, the anchor 133 of the struts 123 points towards the closure disc 11 and can stably pin at different depths in the left atrial appendage, and the seal of the closure 11 to the entrance of the left atrial appendage is ensured.

Fourth Embodiment

Figure 1:
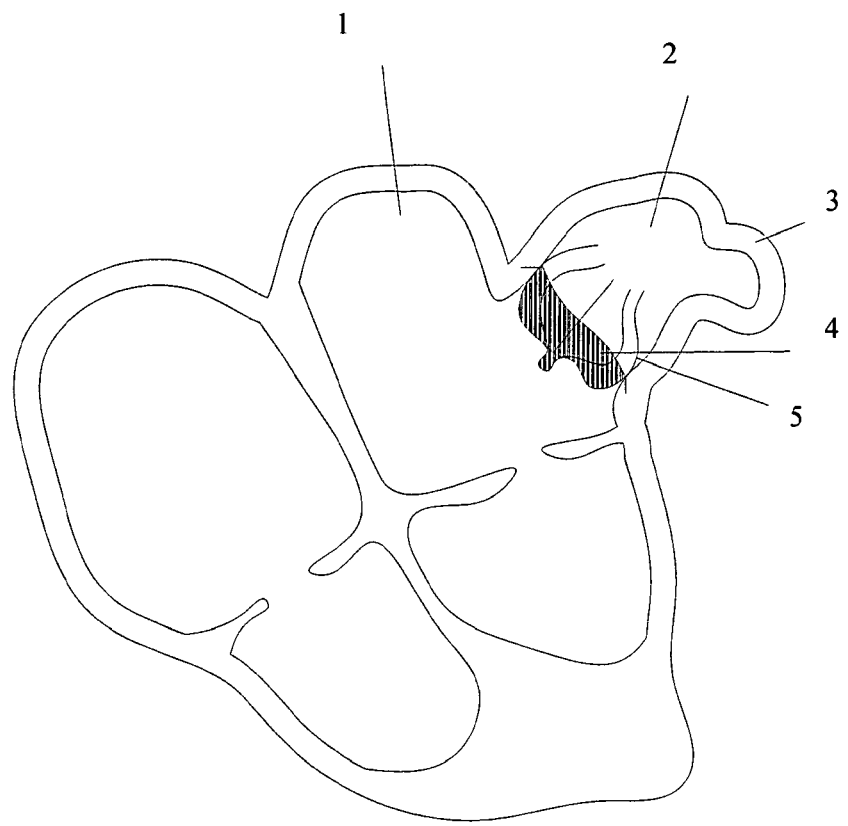
FIG. 1 is a schematic diagram of a position of a plug type left atrial appendage occluder in an anatomical structure of a heart and a left atrial appendage.
Figure 2:
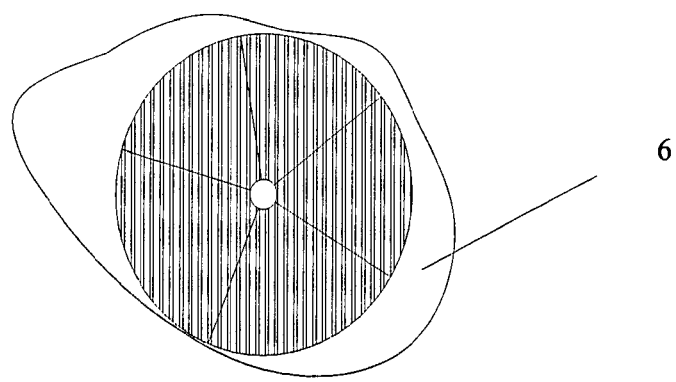
FIG. 2 is a schematic diagram of a position of a plug type left atrial appendage occluder in a left atrial appendage from the direction of the entrance of the left atrial appendage.
Figure 3:
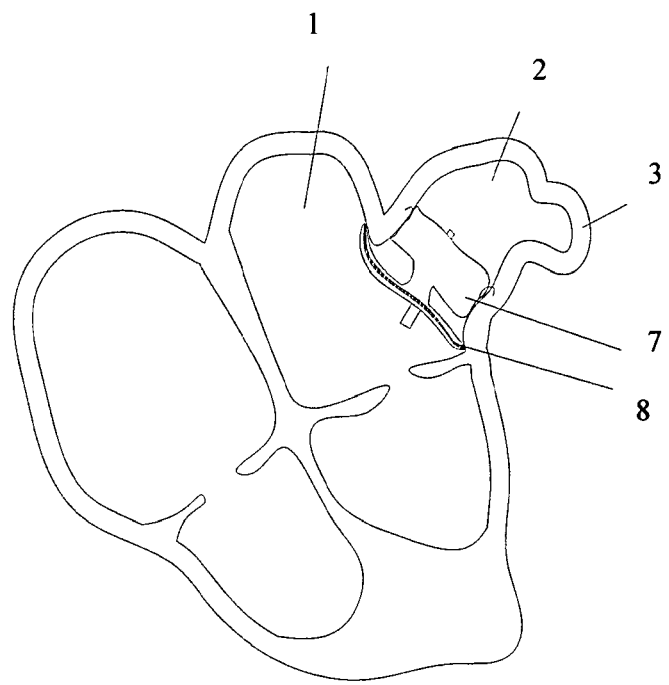
FIG. 3 is a schematic diagram of a position of a plug-and-disc type left atrial appendage occluder in an anatomical structure of a heart and a left atrial appendage.
Figure 4:
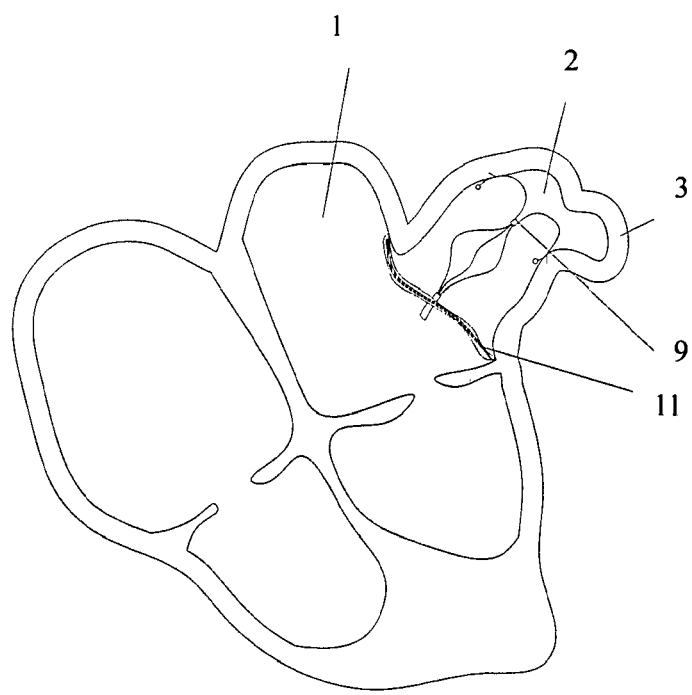
FIG. 4 is a schematic diagram of a position of a left atrial appendage occluder of the invention in an anatomical structure of a heart and a left atrial appendage, in which a fixing frame pins on a deep position of the left atrial appendage.
Figure 16:
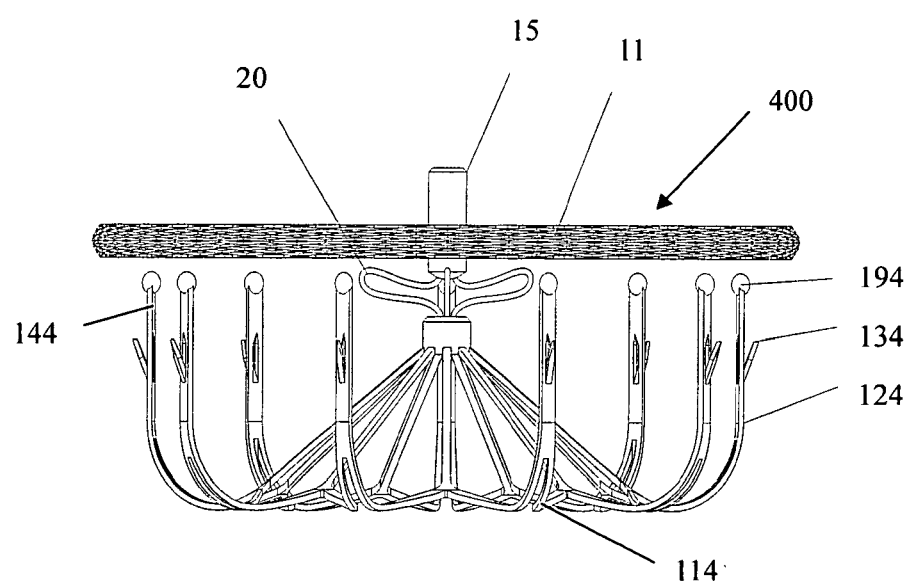
FIG. 16 is a main view of a left atrial appendage occluder according to a fourth embodiment of the present invention.
Figure 17:
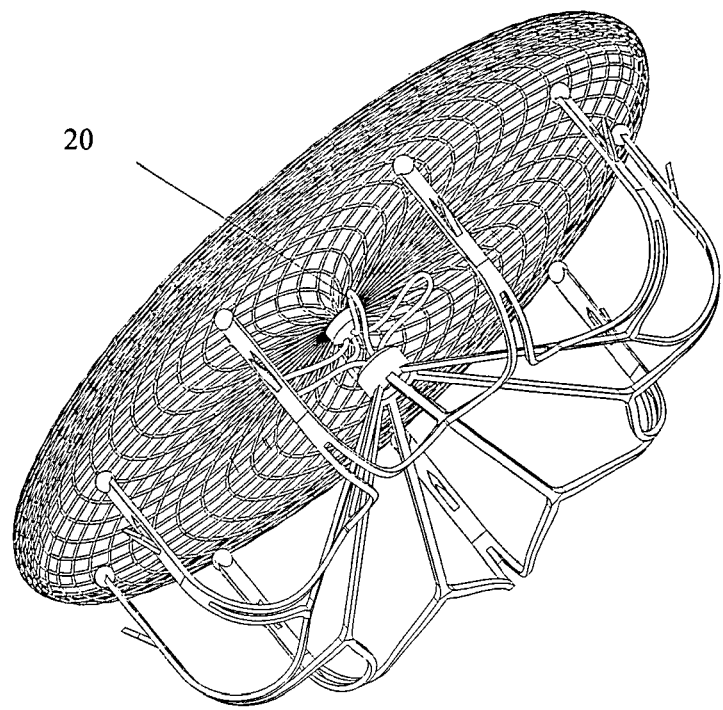
FIG. 17 is a perspective diagram of a left atrial appendage occluder according to a fourth embodiment of the present invention.
Figure 18:
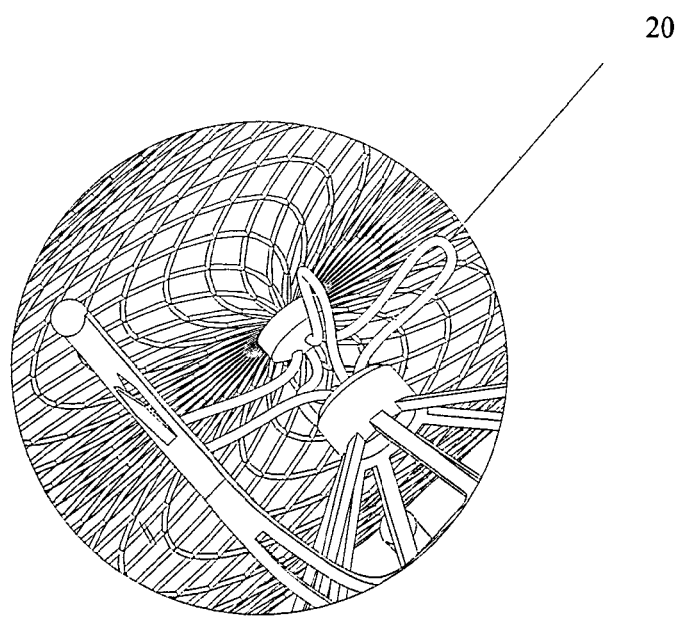
FIG. 18 is a partial enlarged view of part of FIG. 17.

As shown in FIG. 16 to FIG. 18, the left atrial appendage occluder 400 in the fourth embodiment of the invention comprises a closure disc 11 and a fixing frame 114 connected with the closure disc 11. The closure disc 11 is made into a mesh shape via nickel titanium wires by weaving, and then made into a disc shape by heat treatment. Two ends thereof are fixed by sleeves. The sleeve at one end is welded with a connecting member 15 with threads connected with a conveyor. Then, a flow blocking membrane (PTFE or PET membrane) is sutured inside the closure disc 11 via medical suture lines. The other end of the closure disc 11 is a fixed end. The sleeve of the fixed end is connected with a central end of the fixing frame 113. The central end comprises a multi-strand flexible member 20. The top view of the closure disc 11 is the same as shown in FIG. 7 of the first embodiment. Struts 124 of the fixing frame 114 are shaped by cutting and heat treating nickel titanium tubes. Tail ends of the struts 124 are made into bulbs 194 by hot melting, as shown in FIG. 16, to lower the damage of the occluder to the left atrial appendage. During the cutting, the anchor 134 on the fixing frame 114 will also be formed by cutting. The shape of the anchor 134 is formed by a corresponding die, and the anchor 134 points toward the tail end 144 of the strut 124. When cutting the nickel titanium tube, a short section of the nickel titanium tube is still remained at the other end of the fixing frame 114 away from the bulb 194, to avoid the separation of the struts 124 from each other at this end. The multi-strand flexible member 20 is bent into drum-shaped ribs as shown in FIG. 18 via four nickel titanium wires (it may be understood that the number of nickel titanium wires may be less than or more than four; other metal wires may also be used, such as stainless steel wires; each of the nickel titanium wires may be replaced with multiple composite nickel titanium ropes) by heat treatment, because the nickel titanium wires have superelasticity so that the distance between two ends of the multi-strand flexible member 20 may be drawn away. Of course, the multi-strand flexible member 20 may be of other known linear closure structure with the same function as long as all elastic wires are gathered and fixed symmetrically at two ends of this structure, and two ends of the structure have characteristics that they can move relative to each other within a scope permitted by the elastic wires, maintain a shorter distance at the natural state, provide a stable support force and may lengthen the distance under the action of tension. Finally, the closure disc 11 and the fixing frame 114 are connected together by the multi-strand flexible member 20. One end of the multi-strand flexible member 20 is welded with the sleeve at the fixed end of the closure disc 11, while the other end of the multi-strand flexible member 20 is welded with the end of the fixing frame 114 where the nickel titanium tube remains uncut. The multi-strand flexible member 20 has strong deformability and may adjust the relative positions and relative distances between the closure disc 11 and the fixing frame 114 to a large extent. Thus, the anchor 134 of the strut 124 points towards the closure disc 11 and can stably pin at different depths in the left atrial appendage, and the seal of the closure 11 to the entrance of the left atrial appendage is ensured, as shown in FIG. 4 and FIG. 5. In other embodiments of the invention, the diagrams of positions of the left atrial appendage occluder in the anatomical structure of a heart and a left atrial appendage are similar to FIG. 4 and FIG. 5.

Figure 19:
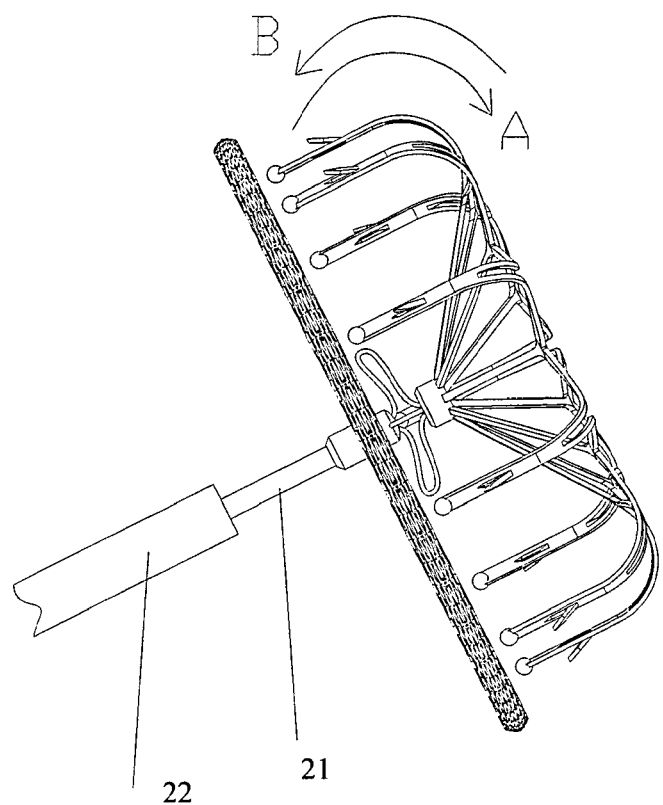
FIG. 19 is a schematic diagram of motion directions of the tail ends of struts when a fixing frame of a left atrial appendage occluder enters a sheath canal and exits from the sheath canal according to the fourth embodiment of the present invention.
Figure 20:
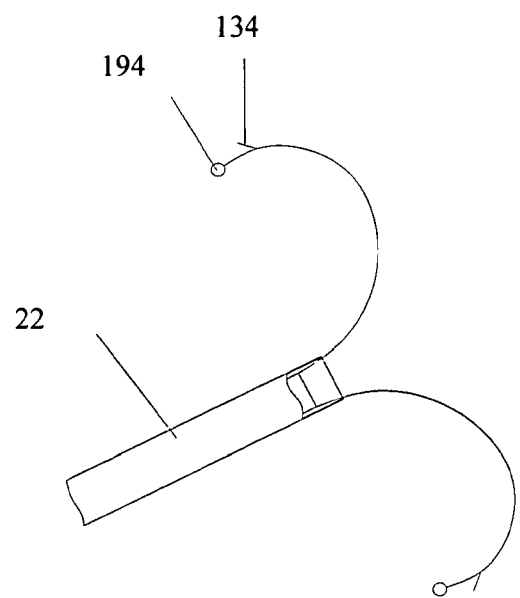
FIG. 20 is a schematic diagram of the state when a fixing frame of a left atrial appendage occluder just enters a sheath canal or just exits from the sheath canal according to the fourth embodiment of the present invention.
Figure 21:
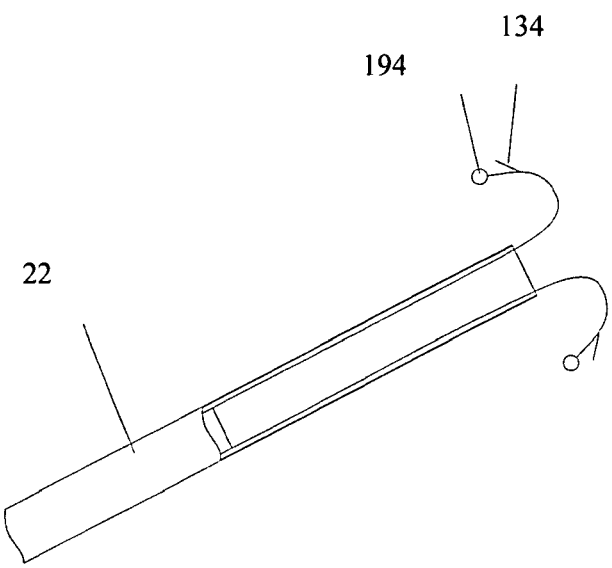
FIG. 21 is a schematic diagram of the state when most parts of the struts of a fixing frame of a left atrial appendage occluder have entered a sheath canal or exited from the sheath canal according to the fourth embodiment of the present invention.
Figure 22:
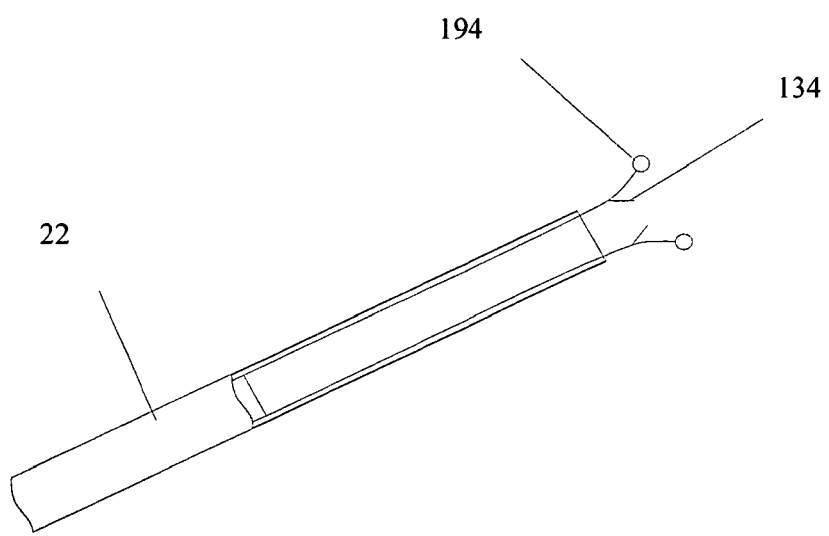
FIG. 22 is a schematic diagram of the state when the tail ends of the struts of a fixing frame of a left atrial appendage occluder are ready to enter a sheath canal or exit from the sheath canal according to the fourth embodiment of the present invention.
Figure 23:
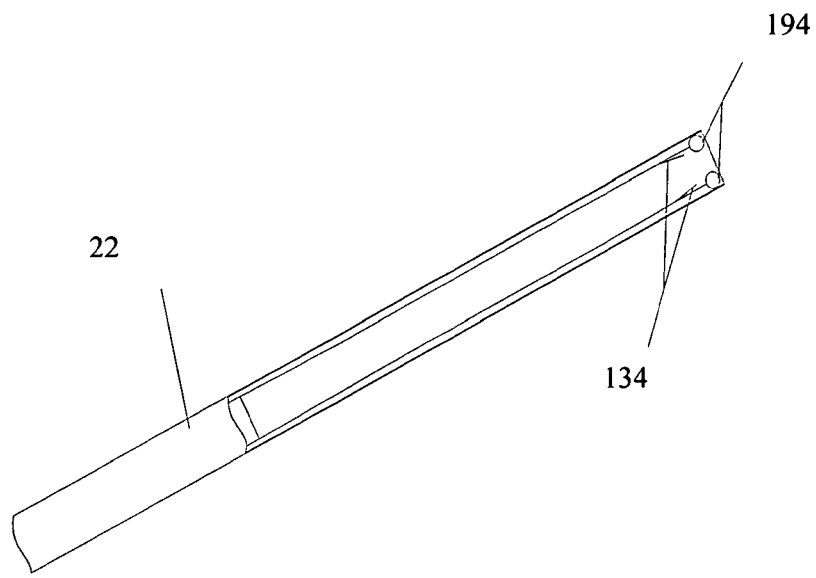
FIG. 23 is a schematic diagram of the state when the tail ends of the struts of a left atrial appendage occluder are in a sheath canal according to the fourth embodiment of the present invention.

As shown in FIG. 19 to FIG. 23, the processes of the fixing frame 114 entering a sheath canal 22 and exiting from the sheath canal 22 have the following characteristics: under the action of a connecting rod 21 of the conveyor, when the fixing frame 114 at the stretched state will retract hack in the sheath canal 22, the tail ends of the struts 124 move along direction A shown in FIG. 19, and different stages of entering the sheath canal 22 are as shown in FIG. 20, FIG. 21, FIG. 22 and FIG. 23 so that the bulbs 194 at the tail ends of each strut 124 and the anchor 134 will do an overturn; when the fixing frame 114 in the sheath canal 22 is pushed out from the sheath canal 22, the tail ends of the struts 125 move along direction B shown in FIG. 19 opposite to all stages of entering the sheath canal 22, and different stages of exiting from the sheath canal 22 will be performed in the order of FIG. 23, FIG. 22. FIG. 21 and FIG. 20; the bulbs 194 at the tail ends of each strut 124 and the anchor 134 will do an overturn opposite to that of entering the sheath canal. Such a design may make the anchor 134 penetrating in the wall of the left atrial appendage and pointing towards the entrance of the left atrial appendage, to be advantageous to avoid falling off of the fixing frame 114. When it is required to withdraw the left atrial appendage occluder 400, the anchor 134 can invert the direction and enter the sheath canal 22 smoothly without damage to the left atrial appendage. Therefore, the left atrial appendage occluder 400 in this embodiment can ensure the good repeated positioning of the fixing frame 114 in the left atrial appendage; i.e., the good repeated positioning of the whole left atrial appendage occluder is ensured. Furthermore, the left atrial appendage occluder lowers the damage of the device to the left atrial appendage and also makes the device applicable to a smaller sheath canal, to be convenient for surgical operations.

Fifth Embodiment

Figure 24:
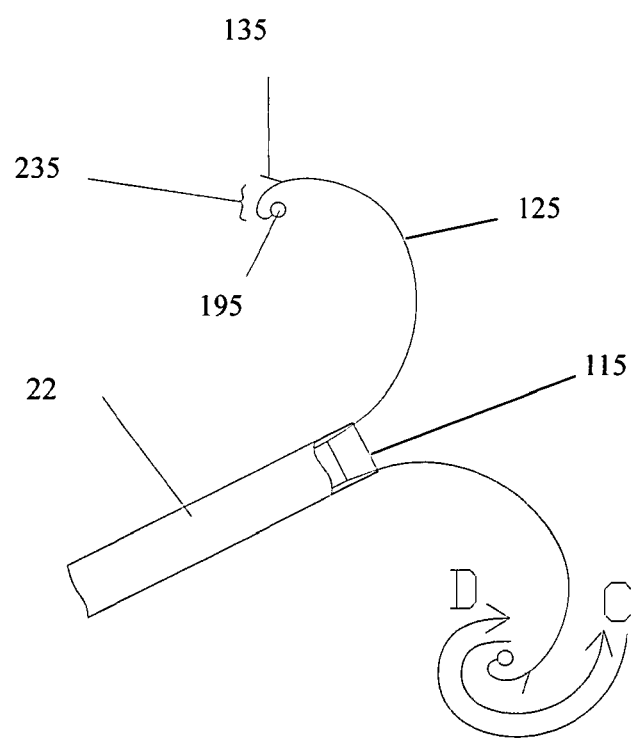
FIG. 24 is a schematic diagram of the state when a fixing frame of a left atrial appendage occluder just enters a sheath canal or just exits from the sheath canal according to a fifth embodiment of the present invention.
Figure 25:
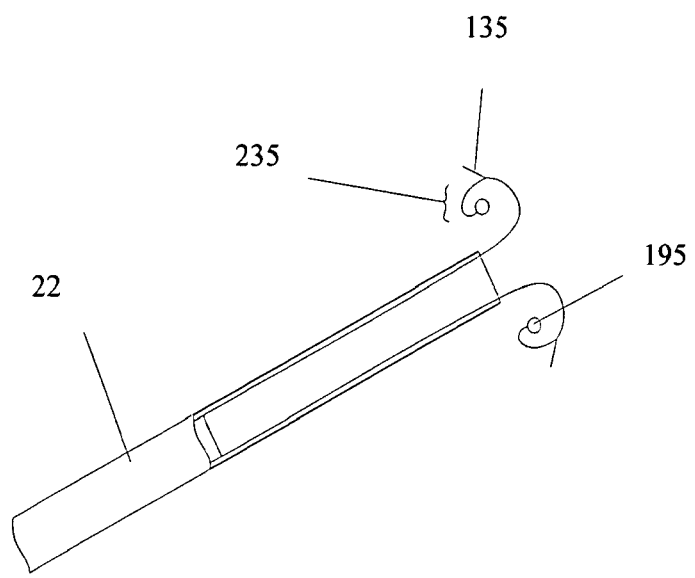
FIG. 25 is a schematic diagram of the state when most parts of struts of a fixing frame of a left atrial appendage occluder have entered a sheath canal or small parts of the struts are to exit from the sheath canal according to the fifth embodiment of the present invention.
Figure 26:
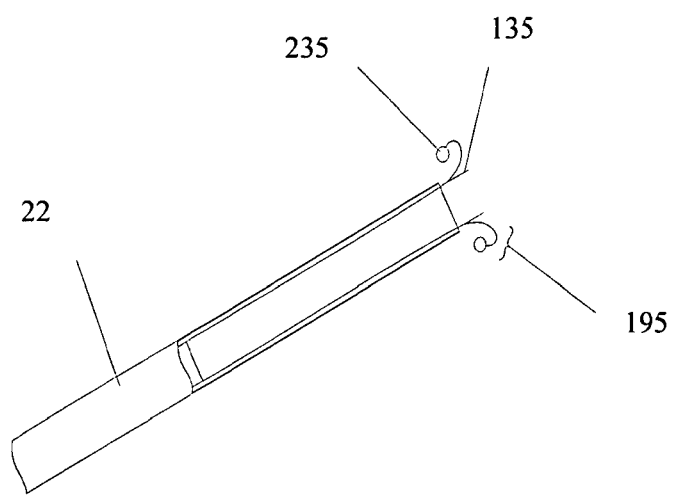
FIG. 26 is a schematic diagram of the state when a U-shaped bent part close to tail ends of struts of a fixing frame of a left atrial appendage occluder is ready to enter a sheath canal or has exited from the sheath canal according to the fifth embodiment of the present invention.

As shown in FIG. 24 to FIG. 26, based on the third embodiment or the fourth embodiment, the difference between the fifth embodiment and the third embodiment or the fourth embodiment is the fixing frame. The fixing frame 115 in the fifth embodiment is roughly similar to the fixing frame in the third embodiment or the fourth embodiment, but the difference is that each strut 125 of the fixing frame 115 in the fifth embodiment is added with a U-shaped bent part 235, and the U-shaped bent part 235 is located between the bulb 195 at the tail end of the strut 125 and the anchor 135. In the state shown in FIG. 24, a part of the fixing frame 115 in this embodiment is retracted in the sheath canal 22, while the tail ends of the struts 125 remain outside the sheath canal 22. In this case, the anchor 135 points basically towards the closure disc 11 (retracted back in the sheath canal and slightly outwards from the axis. The U-shaped bent part 235 is bent towards the center of the fixing frame 115 near from the anchor 135, and the bulbs 195 are fixed at the tail ends of the U-shaped bent parts 235. The tail ends of the struts 125 are hard and have bad stimulation to the contact part of the left atrial appendage, so the struts 125 are added with the U-shaped bent parts 235 which allow the tail ends of the struts 125 avoid contact with the left atrial appendage, and the damage of the expanded occluder in the left atrial appendage to the left atrial appendage is reduced. When manufacturing the fixing frame 115, by using a shaping die of the fixing frame 115, one section of the strut 125 is directly processed into the U-shaped bent part 235 by heat treatment.

The fixing frame 115 in this embodiment is shown as FIG. 24, FIG. 25, FIG. 26, FIG. 22 and FIG. 23 when entering or exiting the sheath canal 22 and has the following characteristics: under the action of a connecting rod 21 of the conveyor, when the fixing frame 115 at the stretched state will retract back in the sheath canal 22, the tail ends of the struts 125 move along direction C shown in FIG. 24, and different stages of entering the sheath canal 22 are in the order as shown in FIG. 24, FIG. 25, FIG. 26, FIG. 22 and FIG. 23; the bulb 195 at the tail end of each strut 125 and the anchor 135 will do an overturn, but the overturn range of the bulbs 195 at the tail ends is larger than that of the anchor 135; when the fixing frame 115 in the sheath canal 22 is pushed out from the sheath canal 22, the tail ends of the struts 125 move along direction D shown in FIG. 24 opposite to all stages of entering the sheath canal 22, and different stages of exiting from the sheath canal 22 will be performed in the order of FIG. 23, FIG. 22. FIG. 26, FIG. 25 and FIG. 24; the bulb 195 at the tail end of each strut 125 and the anchor 135 will do an overturn opposite to that of entering the sheath canal 22, the overturn range of the bulbs 195 at the tail ends is larger than that of the anchor 135. Such a design in this embodiment has many advantages. The anchor 135 on the struts 125 of the fixing frame 115 has the same structure and technical effects as those of the above embodiments, but the U-shaped bent parts 235 near the tail ends of the struts 125 can better avoid the damage of the tail ends of the struts to the left atrial appendage.

The straightened state of the U-shaped bent parts 235 near the tail ends of the struts 125 of the fixing frame 115 in the fifth embodiment is the same as that in FIG. 22, and the state that the tail ends of the struts 125 are completely in the sheath canal 22 is identical to that shown in FIG. 23.

In conclusion, the left atrial appendage occluder is formed by direct connection of an elastic closure disc with a membrane amounted inside it and a fixing frame containing a plurality of struts, or comprises an elastic closure disc with a membrane amounted inside it and a fixing frame connected with the closure disc by a flexible connection structure and provided with a plurality of struts. The whole structure has good stability. The anchor on the struts may turn 180° with the struts, thereby strengthening the anchoring force of the anchor and reducing the damage of the anchor to the left atrial appendage when withdrawing the occluder, also it is advantageous to the repeated positioning of the device and applicable to various structures of left atrial appendage, and the stable positioning may be realized. The tail ends of the struts may realize a 180° or 360° overturn. The bulbs at the tail ends of the struts ensure the successful positioning of the fixing frame and prevent the tail ends of the struts from penetrating through the left atrial appendage. The U-shaped bent parts near the tail ends of the struts further reduce the damage of the occluder to the left atrial appendage. The flexible connection structure may be a spiral structure or a mufti-strand structure, so that the effective adjustment of relative positions and relative distances between the closure disc and the fixing frame is ensured and positioning requirements for different depths of the left atrial appendage of various structures may be realized.

Therefore, the invention has the following advantages:

1. The left atrial appendage occluder has a stable structure and can fit various structures and various sizes of the cavity of the left atrial appendage to the largest extent.

2. It can be positioned on the wall of the left atrial appendage more stably and seal the entrance of the left atrial appendage more closely, considering the balance between the positioning and sealing key effects.

3. The left atrial appendage occluder is easy to position repeatedly and may be withdrawn before being detached from a conveyor. When in surgical operation, a position area can be selected based on the actual shape and size of the patient's left atrial appendage, selection of an improper position area caused by limitations of the device can be avoided and the surgical risk is lowered.

4. The operating steps are simple and smooth, so times of repeated positioning by a doctor is reduced to the largest extent, and the damage to a patient is lowered.

5. The left atrial appendage occluder can fit a small sheath canal, and so the damage of the sheath canal to the patient's vascular wall is lowered.

The above just describes optimal embodiments of the invention, but is not intended to limit the invention. Any modification, equivalent substitution and improvement made within the spirit and principle of the invention should fall into the protection scope of the invention.

The invention claimed is:

1. A left atrial appendage occluder that is delivered to a left atrial appendage by a sheath that has a wall that defines a lumen, comprising:
   a closure disc;
   an elastic fixing frame having a distal end and a proximal end fixed to the closure disc, the fixing frame defining a longitudinal axis, wherein the distal end of the fixing frame extends outwardly from the proximal end and stretches out in a radial direction, and then overturns outwardly towards the proximal end to form a free end when the fixing frame is outside the sheath; and
   at least one anchor, wherein the fixing frame is located between the at least one anchor and the wall of the sheath with the at least one anchor facing radially inwardly towards the longitudinal axis when the fixing frame is in the sheath during delivery, and when the fixing frame is deployed outside the sheath, the at least one anchor outwardly extends from the fixing frame.

2. The occluder of claim 1, wherein the free end of the fixing frame is adjacent to and spaced from the closure disc.

3. The occluder of claim 1, wherein the closure disc and the fixing frame both have a diameter, and the diameter of the closure disc is larger than the diameter of the fixing frame when the occluder is deployed outside the sheath.

4. The occluder of claim 1, wherein the occluder defines a distal end and a proximal end, and the at least one anchor has a free end, and when the fixing frame is in a sheath, the free end of the at least one anchor faces the distal end of the occluder, and when the fixing frame is deployed outside the sheath, the free end of the at least one anchor faces the proximal end of the occluder.

5. The occluder of claim 1, wherein the fixing frame further comprises at least one tail end at the free end, and at least one bent part is located at the tail end and bent inwardly towards the longitudinal axis of the fixing frame.

6. The occluder of claim 5, wherein the at least one bent part is U-shaped.

7. The occluder of claim 6, wherein each U-shaped bent part overturns 360 degrees when the fixing frame is deployed outside the sheath.

8. The occluder of claim 5, wherein the distal end of the fixing frame has an inner surface that faces the proximal end when the occluder is deployed outside the sheath, and an outer surface that faces radially outwardly from the proximal end when the occluder is deployed outside the sheath, and wherein the at least one anchor is provided on the outer surface.

9. The occluder of claim 5, wherein the at least one tail end of the fixing frame is provided with a bulb.

10. The occluder of claim 1, wherein during delivery of the occluder to a left atrial appendage, the fixing frame is released from the sheath before the closure disc is released.

11. The occluder of claim 1, wherein the closure disc is a mesh with two fixed ends, and a flow blocking membrane is disposed on the closure disc.

12. The occluder of claim 11, wherein the flow blocking membrane is inside of the closure disc.

13. The occluder of claim 11, wherein the flow blocking membrane is made of PET or PTFE material.

14. The occluder of claim 1, wherein the closure disc has a distal end, and the proximal end of the fixing frame is around the outside of the distal end of the closure disc.

15. The occluder of claim 1, wherein the length of the at least one anchor on the fixing frame is 1-2 mm.

16. The occluder of claim 1, wherein the proximal end of the fixing frame further comprises a flexible connection structure, and the fixing frame is connected with the closure disc via the flexible connection structure.

17. The occluder of claim 16, wherein the flexible connection structure is a flexible connector with an elastic spiral.

18. The occluder of claim 16, wherein the flexible connection structure is a multi-strand flexible member.

19. The occluder of claim 1, wherein each of the at least one anchor has a root which is disposed on the fixing frame, and each of the at least one anchor has a free end which is automatically splayed outwardly, and the at least one anchor is retracted back to the fixing frame when it is compressed.

20. The occluder of claim 1, wherein the closure disc and the fixing frame are made of nickel titanium alloy.

* * * * *